United States Patent [19]

Bilstad et al.

[11] Patent Number: 4,479,761

[45] Date of Patent: Oct. 30, 1984

[54] ACTUATOR APPARATUS FOR A PREPACKAGED FLUID PROCESSING MODULE HAVING PUMP AND VALVE ELEMENTS OPERABLE IN RESPONSE TO EXTERNALLY APPLIED PRESSURES

[75] Inventors: Arnold C. Bilstad, Deerfield; Richard I. Brown, Northbrook; Robert J. Kruger, Arlington Heights, all of Ill.

[73] Assignee: Baxter Travenol Laboratories, Inc., Deerfield, Ill.

[21] Appl. No.: 453,921

[22] Filed: Dec. 28, 1982

[51] Int. Cl.³ ............................................. A61M 1/03
[52] U.S. Cl. ................................... 417/395; 417/479; 417/510; 128/DIG. 12; 206/364; 206/570; 604/6; 604/153
[58] Field of Search ............... 417/394, 395, 479, 480, 417/510; 128/DIG. 3, DIG. 12; 604/4, 5, 6, 152, 153, 246; 206/570, 571, 572, 364, 365, 366

[56] References Cited

U.S. PATENT DOCUMENTS

| | | |
|---|---|---|
| Re. 27,849 | 12/1973 | Wortman . |
| D. 271,801 | 12/1983 | Preussner . |
| D. 271,802 | 12/1983 | Preussner . |
| 2,980,032 | 4/1961 | Schneider ........................ 417/395 X |
| 3,007,416 | 11/1961 | Childs .............................. 417/479 X |
| 3,148,624 | 9/1964 | Baldwin ........................... 417/479 X |
| 3,154,021 | 10/1964 | Vick ...................................... 417/394 |
| 3,250,224 | 5/1966 | Phillips et al. . |
| 3,298,320 | 1/1967 | Latham ............................ 417/479 X |
| 3,518,033 | 6/1970 | Anderson ............................. 417/478 |
| 3,656,873 | 4/1972 | Schiff ................................... 417/395 |
| 3,689,204 | 9/1972 | Prisk .................................... 417/394 |
| 3,709,222 | 1/1973 | DeVries ............................ 417/395 X |
| 3,741,687 | 6/1973 | Nystroem ......................... 417/395 X |
| 3,771,174 | 11/1973 | Wortman . |
| 3,774,762 | 11/1973 | Lichtenstein ...................... 210/321.3 |
| 3,912,455 | 10/1975 | Lichtenstein ..................... 128/765 X |
| 3,946,731 | 3/1976 | Lichtenstein ................. 128/DIG. 3 |
| 4,042,153 | 8/1977 | Callahan et al. ................. 417/478 X |
| 4,047,844 | 9/1977 | Robinson ......................... 417/395 X |
| 4,121,236 | 10/1978 | Welp et al. . |
| 4,158,530 | 6/1979 | Bernstein ......................... 417/394 X |
| 4,199,307 | 4/1980 | Jassawalla ....................... 417/479 X |
| 4,211,597 | 7/1980 | Lipps et al. . |
| 4,236,880 | 12/1980 | Archibald ........................ 417/479 X |
| 4,250,872 | 2/1981 | Tamari ............................. 417/394 X |
| 4,273,121 | 6/1981 | Jassawalla ....................... 417/479 X |
| 4,277,226 | 7/1981 | Archibald ............................ 417/38 |
| 4,303,376 | 12/1981 | Siekmann ........................ 417/395 X |
| 4,364,716 | 12/1982 | Schjeldahl ........................... 417/394 |
| 4,379,452 | 4/1983 | DeVries .................................. 604/6 |
| 4,411,866 | 10/1983 | Kanno . |
| 4,412,553 | 11/1983 | Kopp et al. . |

FOREIGN PATENT DOCUMENTS 2723197 8/1977 Fed. Rep. of Germany .
2093800 10/1983 United Kingdom .

OTHER PUBLICATIONS

Jeanette Scott, "Membrane and Ultrafiltration Technology", (1980).

Primary Examiner—Leonard E. Smith
Attorney, Agent, or Firm—Paul C. Flattery; Daniel D. Ryan; Eugene M. Cummings

[57] ABSTRACT

A fluid processing apparatus for use in conjunction with a prepackaged disposable fluid processing module of the type which includes an integral housing wherein fluid containers, tubing segments, and other components required in processing a fluid are contained, and wherein fluid communication between the containers, components and tubing segments is provided by a fluid circuit formed within the housing by a first relatively inflexible fluid-impervious sheet member and a second relatively flexible fluid-impermeable sheet member. The fluid circuit includes pump and valve elements which operate in response to pressures applied to the second sheet member. Upon installation of the system in the processing apparatus pneumatic actuator ports apply pressures to the second sheet member through access apertures in the housing to circulate fluid through the fluid circuit.

11 Claims, 30 Drawing Figures

AT REST

FILL STROKE

PUMP STROKE

AT REST

FILL STROKE

PUMP STROKE

AT REST

FILL STROKE

PUMP STROKE

FILL STROKE

PUMP STROKE

ACTUATOR APPARATUS FOR A PREPACKAGED FLUID PROCESSING MODULE HAVING PUMP AND VALVE ELEMENTS OPERABLE IN RESPONSE TO EXTERNALLY APPLIED PRESSURES

BACKGROUND OF THE INVENTION

The present invention relates generally to fluid processing apparatus, and more specifically to processing apparatus for use in conjunction with a self-contained modular fluid processing system operable by application of pressure forces from the exterior of the system housing.

Various methods and apparatus have been developed which utilize disposable single-use processing systems formed of plastics such as vinyl for accomplishing fluid processing procedures. In the medical field, for example, processing systems have been developed for blood fractionation procedures, such as plasmapheresis, leukopheresis and plateletpheresis, wherein whole blood is separated into one or more fractions by means of either a filter element or by means of centrifugation, and for hemodialysis procedures, wherein diffusion exchange occurs through a membrane between whole blood and a dialysis solution.

In these, and in other medical procedures employing disposable fluid processing systems, it is typically necessary for an attendant to first select and locate an appropriate filter or membrane element and one or more flow sets. The packaging of these items must then be opened and the items must be connected together to form a fluid circuit, which is then installed on the particular processing apparatus with which the procedure is to be performed.

Typically, the processing apparatus includes multiple pump, detector and clamping elements on which particular components and tubing segments of the fluid circuit must be individually installed. Consequently, the set-up procedure may be undesirably complex so as to require a specially trained operator, and may require an undesirably long time period to complete. Furthermore, even with the use of a specially trained technician, the potential remains for error, as where the wrong tubing segment is installed on a particular element of the apparatus.

Accordingly, the need has developed in the medical field for a modular fluid processing system and apparatus wherein all of the components required for a particular procedure are contained in a single storable package, and wherein the connections between system components are clearly identified and pre-established so that the system can be quickly set-up. Preferably, such a system and apparatus should be constructed so as to avoid the need for installing individual tubing segments and components of the system on individual pump, monitor and clamp elements of the apparatus. Furthermore, such a fluid processing system should contain all fluid containers necessary for fluids dispensed and collected in the procedure, so that the operator need only install the system in the processing apparatus and connect input and output tubing segments to the donor prior to beginning a procedure.

A system and apparatus which overcomes these difficulties are described in the copending applications of the present inventors, entitled "Prepackaged Fluid Processing Module Having Pump and Valve Elements Operable in Response to Applied Pressures", Ser. No. 453,926, and "Actuator Apparatus for a Prepackaged Fluid Processing Module Having Pump and Valve Elements Operable in Response to Applied Pressures", Ser. No. 453,920, both filed concurrently herewith and assigned to the present assignee. The present application is directed to processor apparatus for use in conjunction with a processing module which differs from this prior system in that it actuable by pressures applied from the exterior of the housing.

The present invention is directed to a fluid processing apparatus for utilization in conjunction with a modular processing system wherein the above requirements are met, and in which can be actuated by forces applied from the exterior of the system housing. The processing apparatus is particularly advantageous in medical procedures where a relatively complex fluid circuit is required in conjunction with a multiple pump, sensing and control elements in the processor apparatus.

The invention is particularly useful in continuous-flow blood fractionation procedures, such as plasmapheresis, wherein plasma (or other blood component) is removed by means of a hollow-fiber filter, and wherein a relatively complex and exacting valving and pumping regimen is required to control blood flow to and from the patient. Accordingly, the invention is illustrated herein in conjunction with a blood fractionation circuit, although it will be appreciated that the invention can be configured to provide other fluid circuits for other medical and non-medical procedures.

Accordingly, it is a general object of the present invention to provide a new and improved fluid processing apparatus.

It is a further object of the present invention to provide a fluid processing apparatus wherein the components and interconnections required in an associated fluid processing module are contained within the system housing and actuable in response to forces applied from the exterior thereof.

It is a further object of the present invention to provide a fluid processing apparatus for use with a processing module which includes an integral housing for storing the principal components thereof, and wherein fluid-impermeable plastic sheet members within the housing form a fluid circuit actuable from the exterior of the housing for interconnecting the various components and tubing segments of the module.

SUMMARY OF THE INVENTION

The invention is directed to processor apparatus for use in conjunction with a fluid module for performing a fluid procedure. The module includes a housing. First and second fluid-impermeable sheet members within the housing form a fluid circuit which includes an element actuable by a force applied to the second sheet member. Access apertures in the housing enable force to be applied by the processor apparatus to the second sheet member to actuate elements in the fluid circuit.

BRIEF DESCRIPTION OF THE DRAWINGS

The features of the present invention which are believed to be novel are set forth with particularity in the appended claims. The invention, together with the further objects and advantages thereof, may best be understood by reference to the following description taken in conjunction with the accompanying drawings, in the several figures of which like reference numerals identify like elements, and in which:

DESCRIPTION OF THE PREFERRED EMBODIMENT

Figure 1:
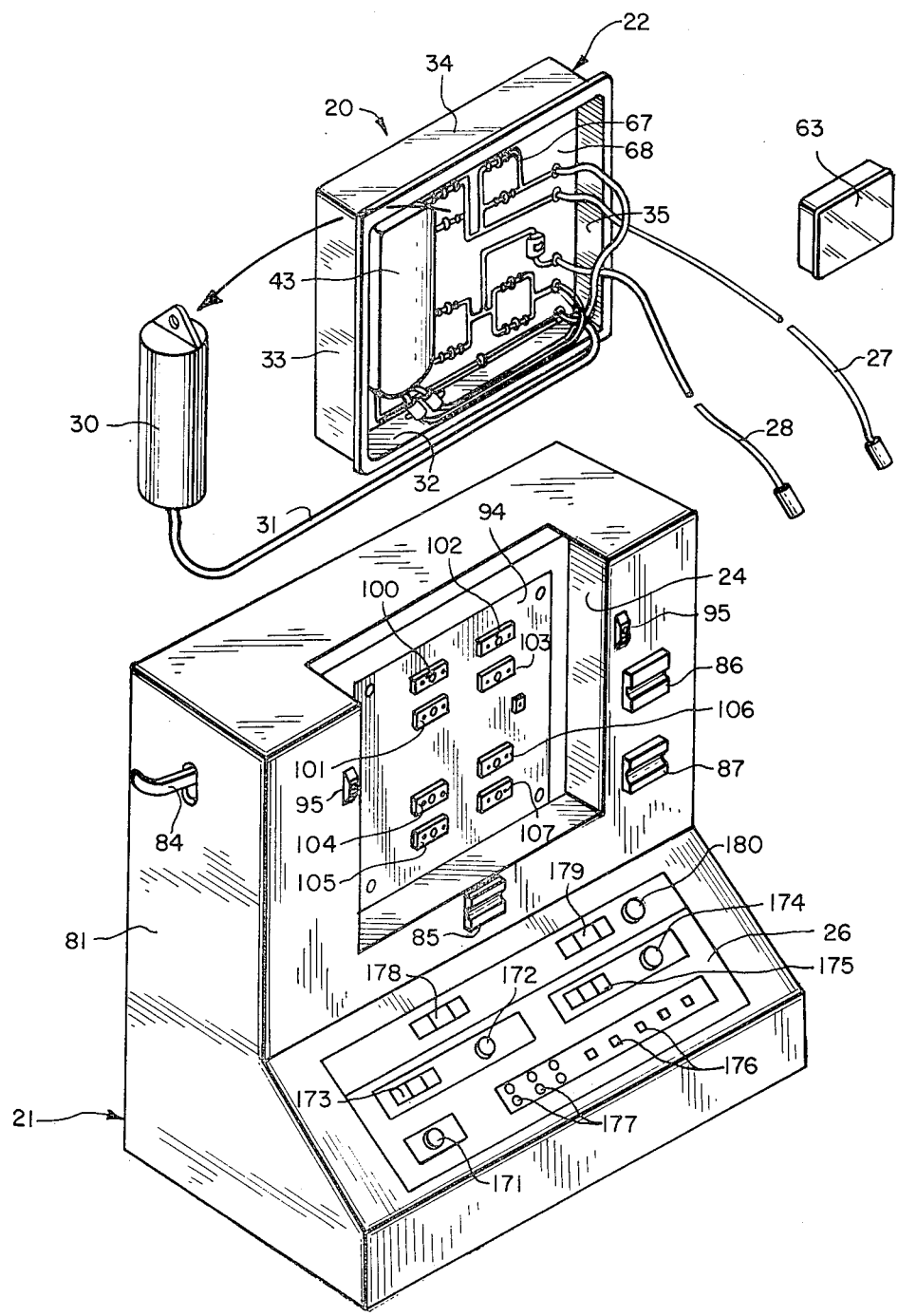
FIG. 1 is a perspective view of a processing apparatus and associated processing module constructed in accordance with the invention, disassembled and positioned for installation, for providing a continuous flow separation of plasma from whole blood.
Figure 2:
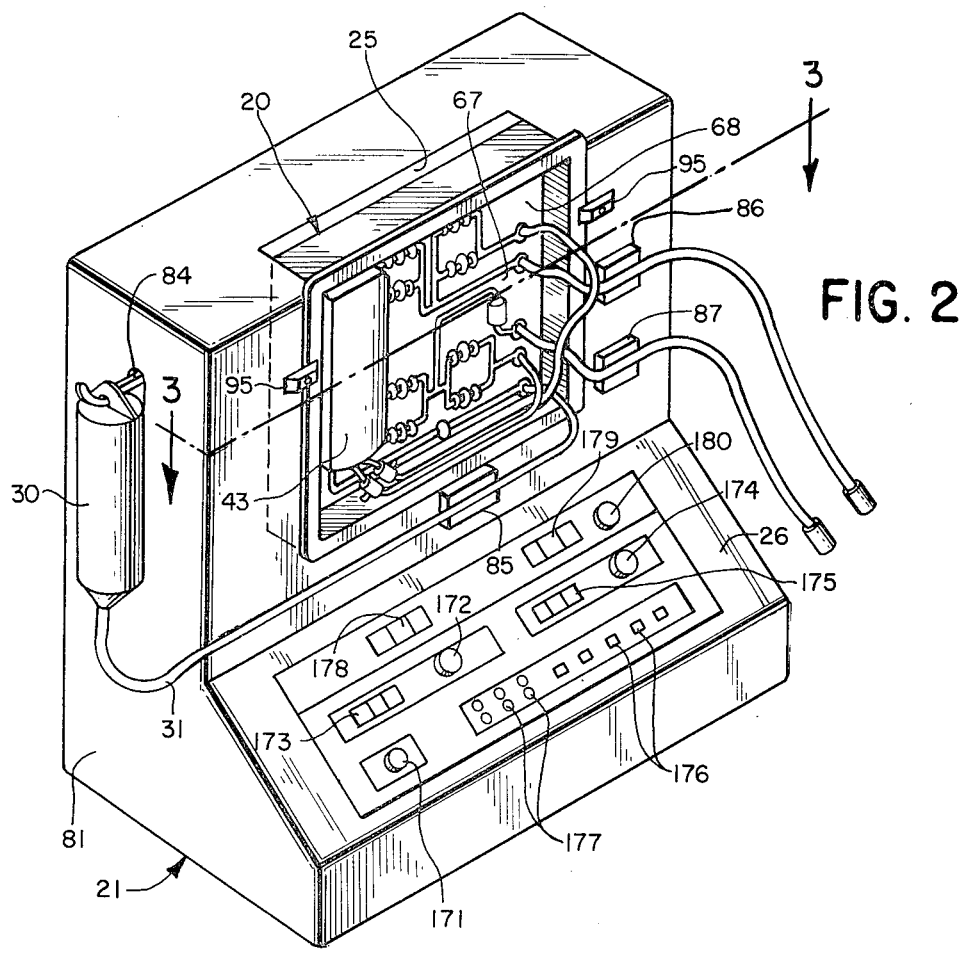
FIG. 2 is a perspective view of the processing apparatus showing the associated processing module installed in the processing apparatus actuator station.
Figure 3:
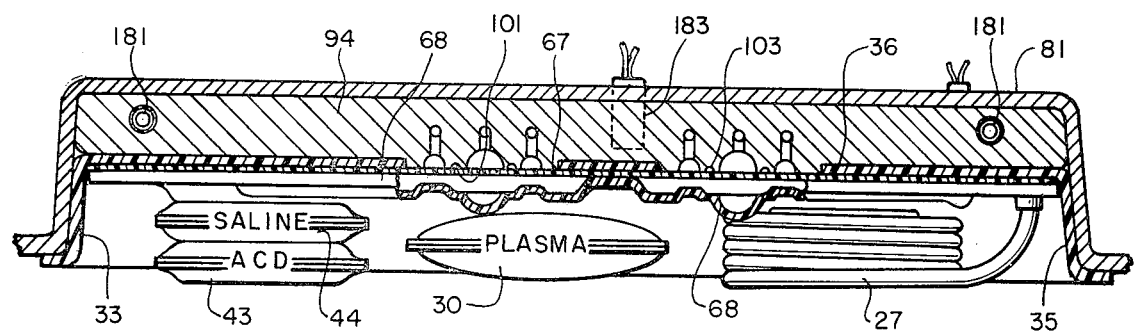
FIG. 3 is a cross-sectional view of the processing module and actuator station of the processing apparatus taken along line 3—3 of FIG. 2.
Figure 4:
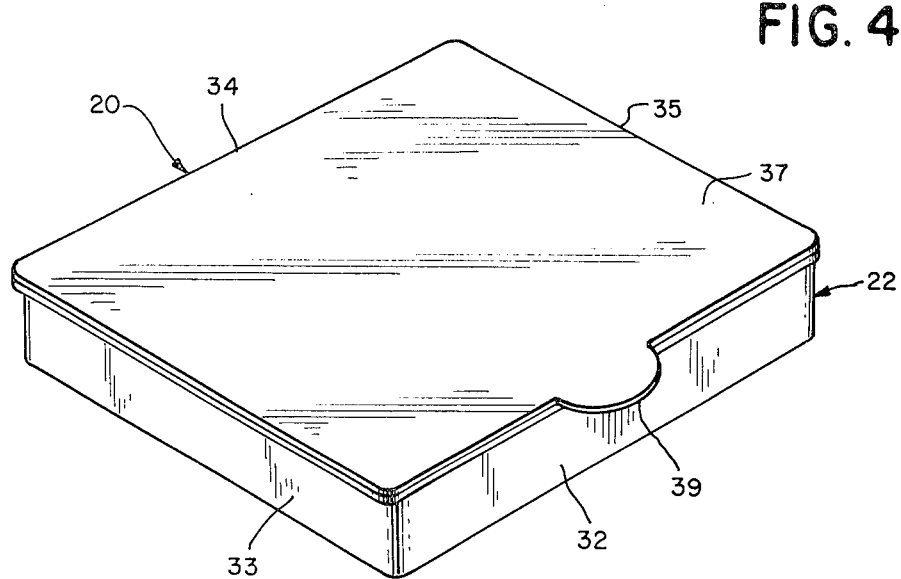
FIG. 4 is a perspective view of a modular fluid processing system for use in conjunction with the processing apparatus of the invention for performing continuous-flow plasmapheresis, showing the cover thereof in place and the system configured for long term storage.

Referring to the drawings, and particularly to FIGS. 1-3, a unitary fluid processing module 20 is shown for performing a plasmapheresis procedure in conjunction with a processor apparatus 21 constructed in accordance with the invention. The disposable processing module, which is described in the copending application of the present inventors, entitled "Prepackaged Fluid Processing Module Having Pump and Valve Elements Operable in Response to Externally Applied Pressures", Ser. No. 453,922, filed concurrently herewith, includes an integral housing 22 wherein the principal components of the module are contained and pre-connected. In use, the components are removed from the housing, and the housing is installed in an actuator station 24 in the processor apparatus, wherein pumping and valving actions necessary to accomplish the plasmapheresis procedure are provided in accordance with parameters established by the operator on a control panel 26. During the procedure whole blood is received from a donor through a tubing segment 27 and returned to the donor through a tubing segment 28. Plasma is collected in a plasma container 30 suspended from the processor apparatus and connected to the system by a tubing segment 31.

Figure 5:
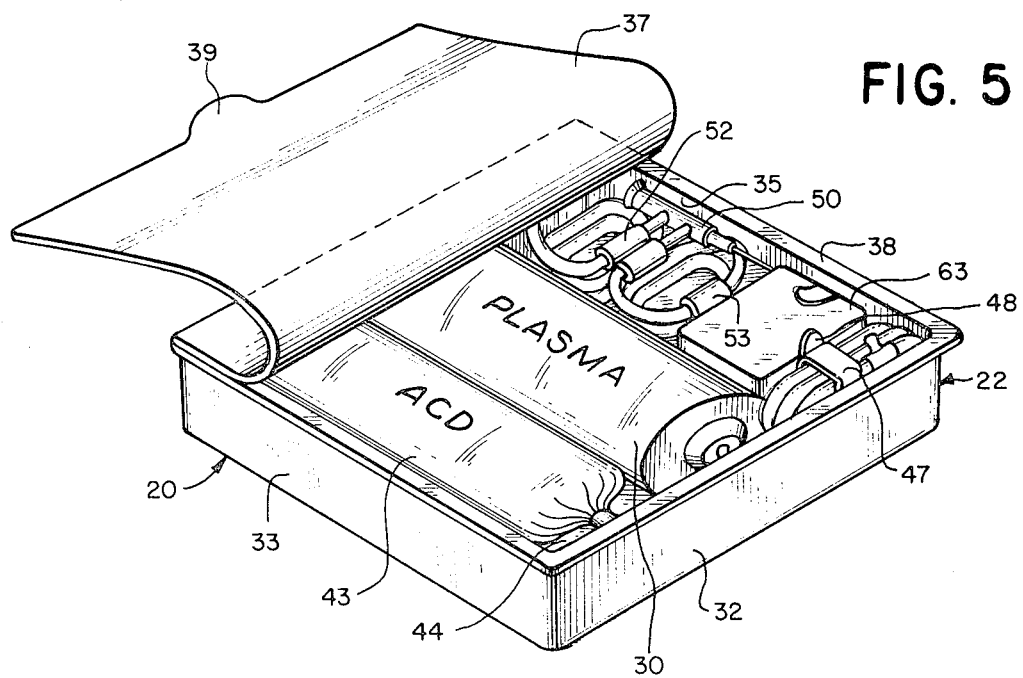
FIG. 5 is a perspective view of the processing system with the cover substantially removed to show the placement of the principal components of the module therein.

Referring to FIGS. 4-8, the housing 22 of the fluid processing module is seen to comprise four side panels 32-35 and a bottom panel 36 formed of a relatively rigid fluid-impermeable material, such as molded plastic. The housing is closed and sealed for long term storage by means of a cover 37, which is sealed over the open end of the housing. The cover may be formed of a flexible fluid-impervious material such as metallic foil or vinyl, and may be secured by means of a layer 38 of adhesive or other appropriate means to the edge of the tray, as shown in FIG. 5. The housing side panels 32-35 preferably each include an outwardly projecting rim portion to facilitate this attachment. A pull tab 39 may be provided to assist the operator in removing the cover.

The interior of housing 22 contains the components required for performing the particular procedure for which the processing system is designed. In the context of a continuous flow plasmapheresis procedure, containers are required for storing an anticoagulant solution (such as ACD or CPDA), a saline solution, and the collected plasma. Accordingly, the fluid processing system located within the housing in the illustrated embodiment includes a prefilled ACD container 43, a prefilled saline container 44 and the empty plasma collection container 30.

The prefilled ACD container 43 and saline container 44 are preferably formed of flexible vinyl material. To prevent the contents of the containers 43 and 44 from evaporating through the vinyl walls of the containers, a suitable overwrap (not shown) is preferably provided to form a vapor barrier around the containers.

The containers 43 and 44 may be stored within housing 22 in a normally unattached condition with the associated fluid circuit. In this arrangement, at the time of use, the containers 43 and 44 are removed from the housing 22, the overwraps are removed, and the containers are then connected by the operator in flow communication with the circuit. In making the connection, a conventional blood "spike" can be used to pierce a membrane associated with the inlet port of the end container. Alternately, a sterile connector device can be used to interconnect the containers 43 and 44 with the fluid system, such as disclosed in Granzow, U.S. Pat. No. 4,157,723.

Preferably, the containers 43 and 44 are stored within the housing in a preattached condition with the fluid circuit. The containers 43 and 44, along with the associated overwraps may be integrally connected with the circuit using a port block, such as disclosed in Boggs et al, U.S. patent application Ser. No. 282,894, filed July 13, 1981 and entitled "Port Block Assembly for Interconnecting a Fluid Container with a Fluid Conduit". In this arrangement, the containers 43 and 44 are preferably permanently secured within housing 22 by adhesive attachment to the interior surface of the adjacent side panel 34.

When in a preattached condition, the ACD container 43 is integrally connected to the fluid circuit of the processing system by a tubing segment 56 which includes a frangible in-line cannula 57 (see FIG. 8), such as one disclosed in Bayham et al, U.S. Pat. No. 4,294,247. This cannula 57 is preferably arranged so as to be readily accessible to the operator upon removing cover 37, and preferably also includes a pull tab 58 containing indicia and/or color coding to draw the operator's attention to the cannula 57 during the set-up procedure.

Similarly, when preattached, the saline container 44 is integrally connected to the fluid circuit by means of a tubing segment 60 which includes another frangible in-line cannula 61. This cannula 61 is also preferably positioned for ready access to the operator upon removing cover 27, and also includes a pull tab 62 containing indicia and/or color coding to assist the operator in locating and fracturing the cannula during set-up.

Figure 8:
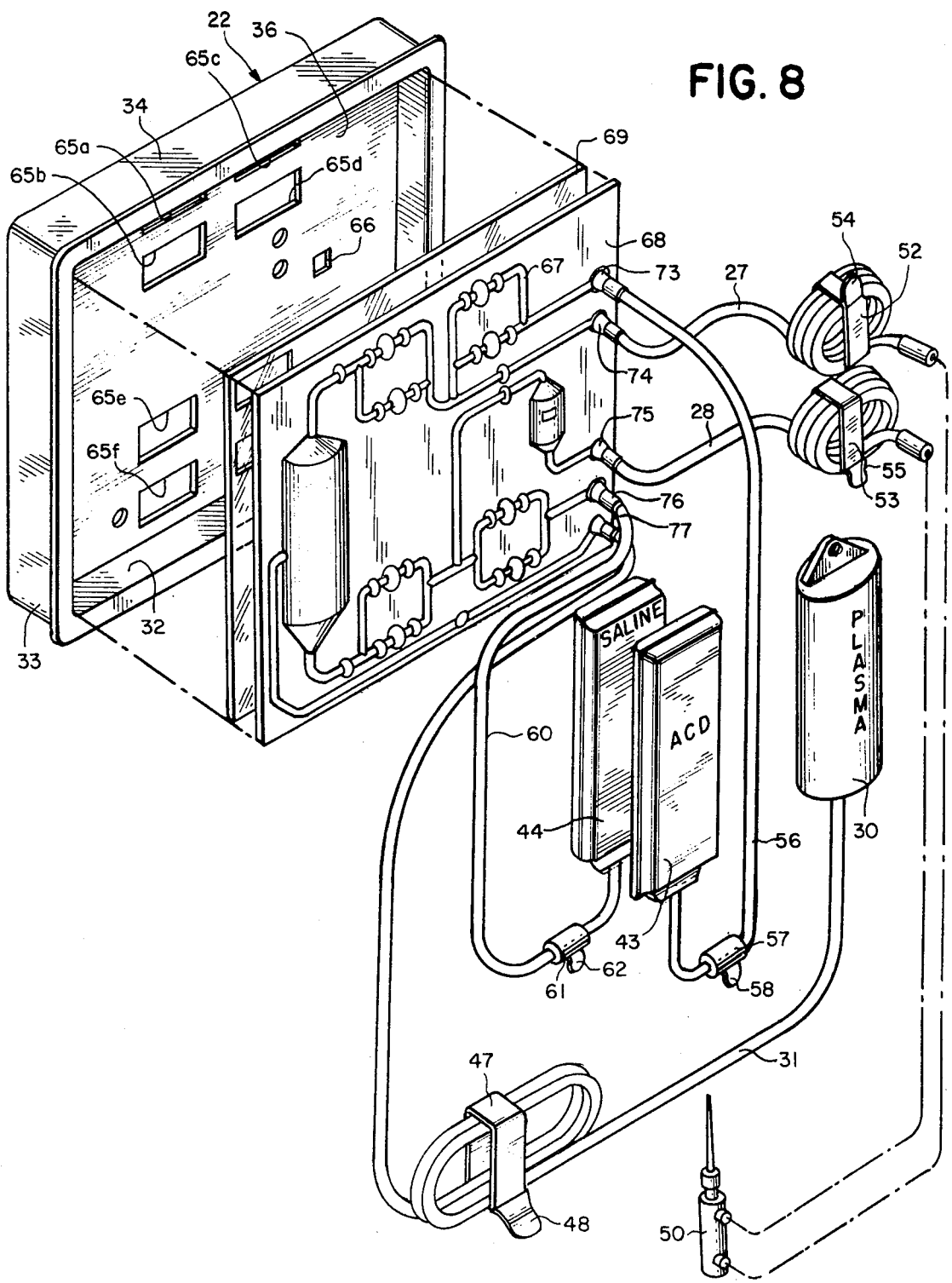
FIG. 8 is an exploded perspective view of the processing module showing the principal components and interconnections thereof.

Plasma container 30, which may be in the form of an unbreakable bottle of the type which conforms to standards established for long term plasma storage, is preferably not permanently secured and can be removed by the system operator at time of use. As is best shown in FIG. 8, tubing segment 31 is preferably prearranged in a compact bundle in housing 22 and secured by an adhesive strip 47 or other appropriate means to an adjacent side panel 32 (see FIG. 5) so as to be readily accessible when preparing the processing system for use. A pull tab 48 bearing appropriate indicia and/or color coding may be provided at one end of adhesive strip 47 to facilitate removing the strip from the tubing bundle.

Tubing segments 27 and 28 are each connected at one end to the processing circuit, and at their other end to respective ports of a conventional dual lumen phlebotomy needle 50 to accommodate a "single needle" plasmapheresis procedure. Alternately, each tubing segment 27 and 28 could individually communicate with a separate phlebotomy needle to accommodate a "two needle" plasmapheresis procedure.

Tubing segments 27 and 28 are also each preferably prearranged in a compact coil within housing 22 and secured by respective adhesive strips 52 and 53 in this form. Pull tabs 54 and 55 identified by appropriate indicia and/or color coding may be provided to assist the operator in locating and removing the adhesive strips from the tubing segment coils.

ACD container 43 is connected to the fluid circuit of the processing system by a tubing segment 56 which includes a frangible in-line cannula 57. This cannula is preferably arranged so as to be readily accessible to the operator upon removing cover 37, and preferably includes a pull tab 58 containing indicia and/or color coding to draw the operator's attention to the cannula during the set-up procedure. Saline container 44 is connected to the fluid circuit by means of a tubing segment 60 which includes a frangible in-line cannula 61. This cannula is preferably positioned for ready access to the operator upon removing cover 27, and includes a pull tab 62 containing indicia and/or color coding to assist the operator in locating and fracturing the cannula during set-up.

Additional components and items required during the plasmapheresis process are contained within a small rectangular miscellaneous components container 63 disposed within housing 22. This container may include hypodermic needles, bandages, surgical tape, antiseptic solution, and other items incidental to the procedure.

Figure 7:
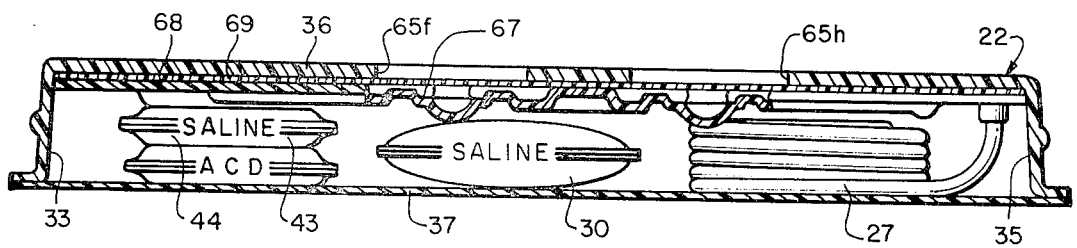
FIG. 7 is a cross-sectional view of the processing module taken along line 7—7 of FIG. 6.

As shown in FIG. 7, the ACD and saline containers 43 and 44 are generally wide and relatively flat so as to permit stacking one-above-the-other within housing 22. The plasma container 30, which as previously developed is preferably in the form of a standard plasma collection bottle, is positioned to one side of the stacked saline and ACD containers so as to allow room for tubing coils 27, 28 and 31, and the miscellaneous supplies container 63.

Figure 6:
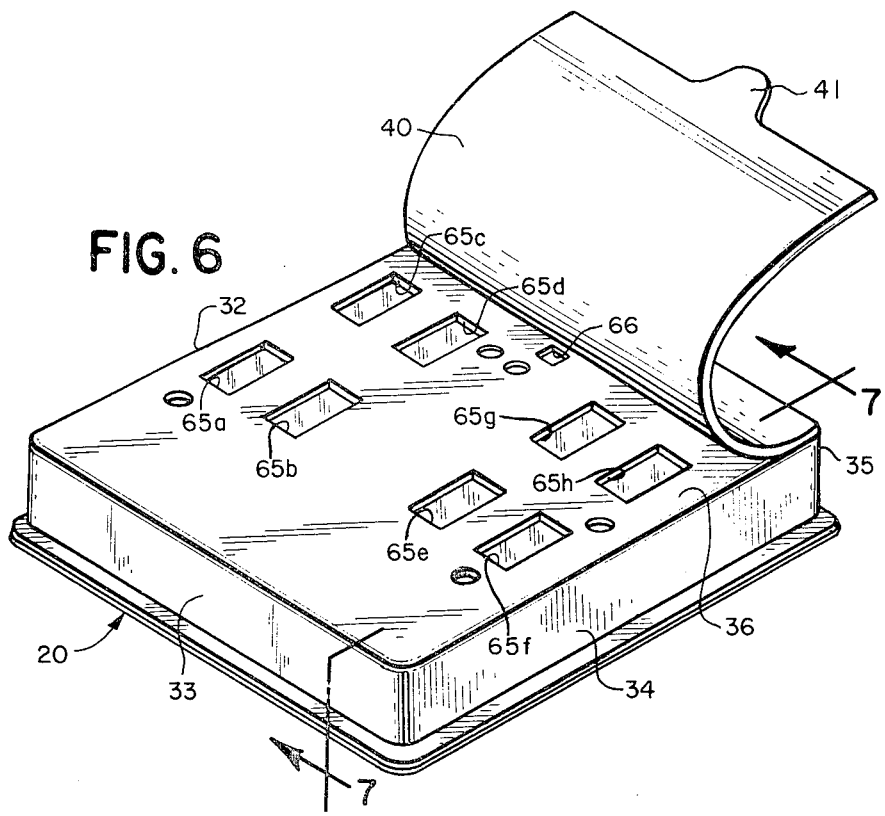
FIG. 6 is a perspective view of the bottom of the fluid processing module showing the actuator access apertures provided on the bottom panel thereof.

As shown in FIGS. 6 and 7, the bottom panel 36 of housing 22 is molded to include eight apertures 65a–65h which provide access to pump and valve components contained within the fluid circuit of the processing system. An additional aperture 66 provides access to a fluid absence detector in the fluid circuit.

Figure 11:
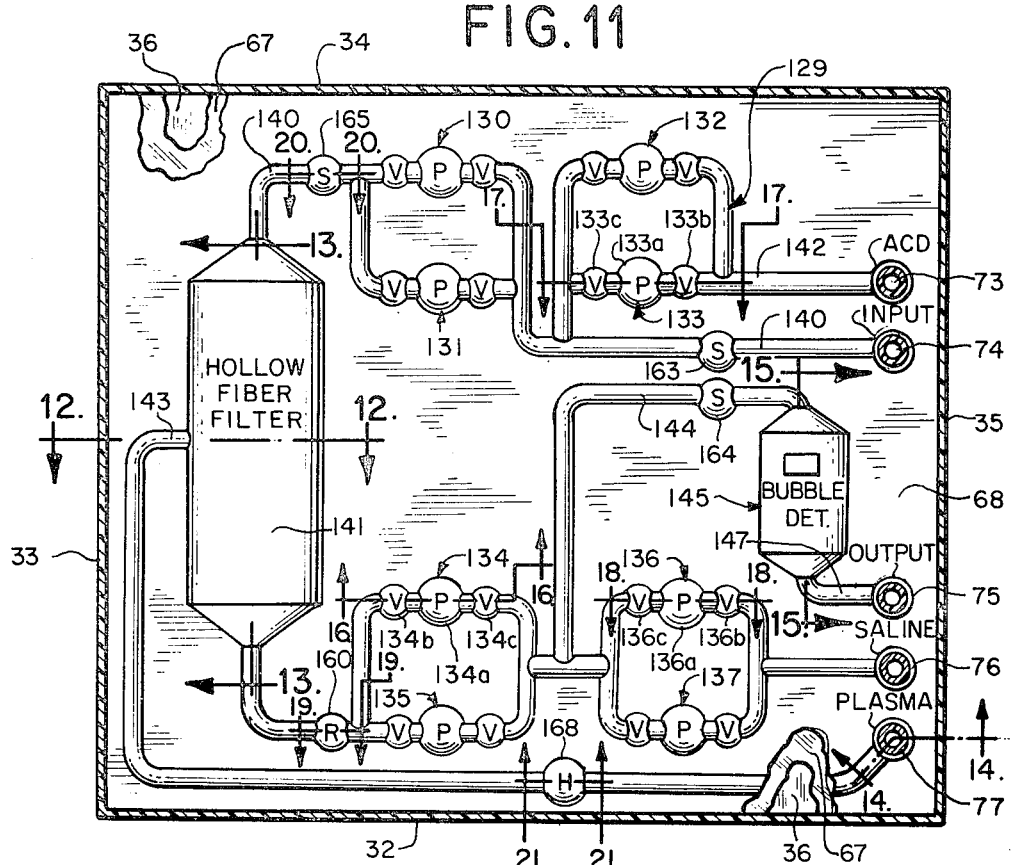
FIG. 11 is a front elevational view of the overlying fluid-impermeable flexible sheet member of the processing system partially fragmented to show the underlying flexible sheet member and the bottom panel of the housing.

Referring to FIGS. 8 and 11, a fluid circuit for interconnecting containers 30, 43 and 44 and the other components of the system and for providing necessary pumping, valving and sensing elements in the system, is provided by a raised portion 67 on a relatively stiff fluid-impervious plastic sheet member 68, and an underlying relatively flexible plastic sheet member 69 fitted between sheet member 68 and bottom panel 36. The plastic sheet members are preferably dimensioned to correspond to the inside peripheral dimensions of the bottom panel and secured to the panel and to each other by thin layers of adhesive so as to form a fluid-sealed fluid circuit within the processing system.

Fluid communication is established with the fluid circuit by means of five connector fittings 73–77 which extend through respective apertures in plastic sheet member 68. Tubing segment 56 is connected to connector 73 at one end and to the ACD container 43 at its other end. Tubing segment 27 is connected at one end to connector 74 and at its other end to the needle adapter 50. Tubing segment 28 is connected to connector 74 at one end and to needle 50 at its other end. Tubing segment 60 is connected between connector 76 and saline container 44. Tubing segment 31 is connected between connector 77 and plasma collection container 30.

Thus, each of the components contained within housing 22 is interconnected as required for the plasmapheresis procedure. No additional interconnections need be made by the operator during set-up.

As shown in FIGS. 1 and 2, in setting-up processing system 20 plasma collection container 30, tubing segments 27, 28 and 31, and the accessories container 63 are removed from housing 22. The system is then installed in processor apparatus 21, which provides fluid pumping, valving and monitoring functions necessary in accomplishing the plasmapheresis procedure. These functions are accomplished without the necessity of individually installing tubing segments and other components of the system in separate pumping, valving and sensing elements of the apparatus. Instead, upon installation of the processing system in the actuator station 24 of the processor apparatus, all such functions are realized automatically without individual attention by the operator and without interrupting the integrity of the fluid circuit of the processing system.

In accordance with the invention, processing apparatus 21 provides fluid pumping and valving functions by application of pressure forces to the flexible sheet member 69 through apertures 65a–65h in the bottom panel 36 of housing 22. To this end, processing apparatus 21 includes a housing 81 having a generally vertical portion within which the actuator station 24 is provided for receiving housing 22, and a lower base portion on which control panel 26 is provided. A hanger arm 84 is provided on the left (as viewed in FIG. 1) side of the upper housing portion to support the plasma collection container 30, and three tubing retention blocks 85–87 are provided for supporting respective ones of tubing segments 31, 27 and 28 when housing 22 is seated in station 24.

In operation, pressure communication with the processing module is established by actuator station 24. When housing 22 is installed in station 24, eight individual valve actuator elements extend through respective ones of apertures 65a–65h in bottom panel 36 so as to engage sheet member 69.

Figure 10:
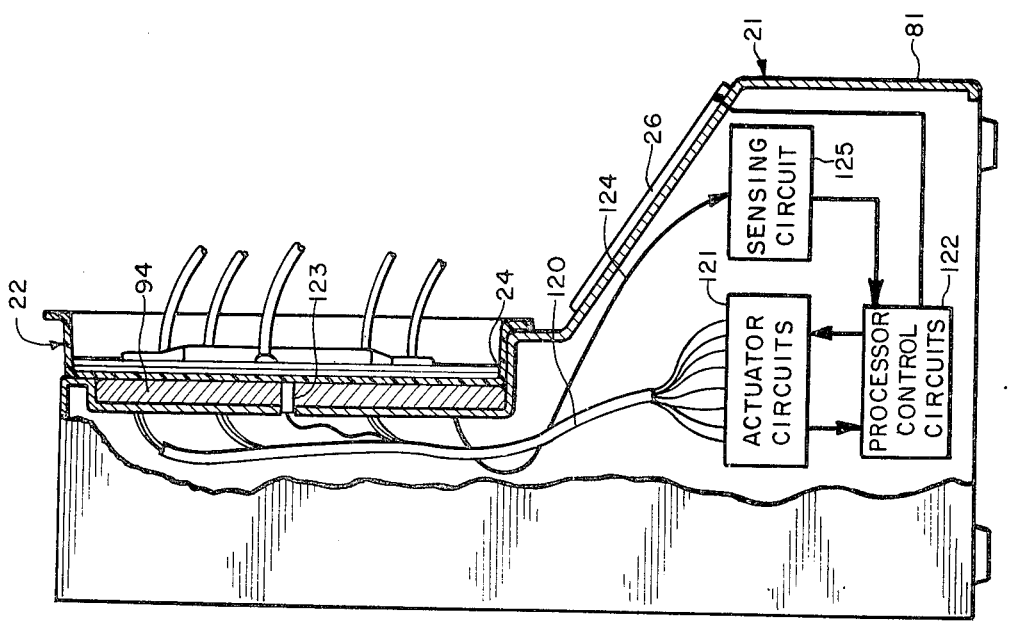
FIG. 10 is a side view, partially cross-sectional and partially diagrammatic, of the processor apparatus showing the actuator station thereof, and the principal control circuits incorporated within the processor apparatus.

As shown in FIGS. 3 and 10, the actuator station 24 includes an actuator plate 94. This actuator plate includes eight pneumatic pump actuator elements 100–107 which apply a vacuum and/or pressure control effect to portions of sheet member 69 associated with corresponding pump elements in the fluid circuit defined by that sheet member and sheet member 68 to obtain necessary pumping and valving functions. The actuator plate 94 is mounted within actuator head 25 by means of a plurality of machine screws 108, or other appropriate means, so that the actuator plate can be removed and a different actuator plate having a different arrangement of vacuum actuator ports can be substituted when reconfiguring the processor apparatus for a different fluid processing procedure. A pair of retaining clamps 95 may be provided for holding module 20 in actuator station 24.

Referring to FIG. 10, within actuator plate 94 the individual pneumatic actuator elements 100–107 are connected by respective tubing segments collectively indicated as 120 to actuator circuits 121. These actuator circuits respond to electrical command signals issued by a processor control circuit 122 within processor apparatus 21 to apply a vacuum or pressure differential at the actuator ports, as required in performing the fluid processing procedure. Also, one or more sensing elements such as an ultrasonic transducer 123 may be provided in the actuator station to sense the occurrence of a fluid absense in the fluid circuit. This detector may be connected by a conductor 124 to appropriate sensing circuits 125 within the apparatus, which provide an appropriate output signal to control circuits 122 upon the occurrence of a fluid absence. In addition, control circuits 122 may receive operator-initiated command signals from control panel 26.

The fluid circuit formed between sheet members 68 and 69, which is collectively identified by the number 129 in FIG. 11, is seen to comprise eight pump elements 130–137 for establishing flow through the fluid circuit. These pump elements, which are actuated by respective ones of actuator elements 100–108 in actuator plate 94, operate in pairs, each pair member being alternately actuated to establish a continuous flow of fluid. Pump elements 130 and 131 are paired to pump whole blood, as received from a donor through tubing segment 27 and connector 74, through a conduit segment 140 to a filter element 141. Pump elements 132 and 133 are paired to pump anticoagulant (ACD) fluid from tubing segment 56 and connector 73 through a conduit segment 142 into conduit segment 140, wherein it is combined with whole blood. Within filter element 141 plasma is separated, and separately supplied to port 77 through a conduit segment 143. Pump components 134 and 135 pump plasma-deficient whole blood from filter element 141 through a conduit segment 144 to a fluid absence detector element 145. Pump elements 136 and 137 operate to combine saline from tubing segment 60 and connector 76 through a conduit segment 146 to the plasma-deficient blood in conduit segment 144. Plasma-deficient blood from fluid absence detector element 145 is supplied through a conduit segment 147 to connector 75 and tubing segment 28 for return to the donor.

Figure 12:
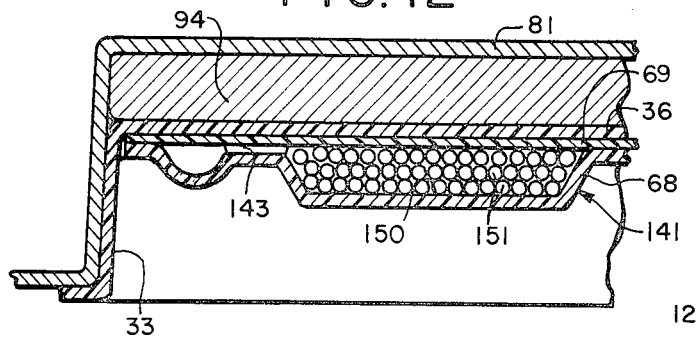
FIG. 12 is a transverse cross-sectional view of the hollow-fiber filter element of the flow system taken along line 12—12 of FIG. 11.
Figure 13:
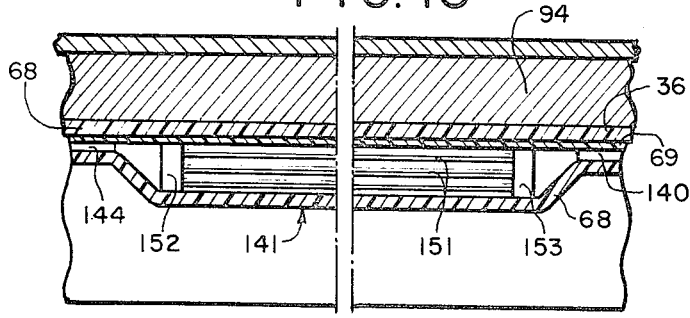
FIG. 13 is a longitudinal cross-sectional view of the filter element taken along line 13—13 of FIG. 11.

Referring to FIGS. 12 and 13, the plasma filter element 141 comprises a chamber 150 within which a plurality of hollow fiber filter elements 151 are arranged side-by-side in a longitudinal bundle to convey fluid received from conduit segment 140 to conduit segment 144. Adjacent each end of the filter bunder layers 152 and 153 of a fluid-impermeable material such as polyurethane are deposited to form liquid barriers which prevent fluid flow except through the hollow fibers of the filter. Plasma collected in the space surrounding the hollow fiber filter elements is conveyed through conduit segment 143 to connector 77 and tubing segment 46 for collection in the plasma collection container 30.

Figure 14:
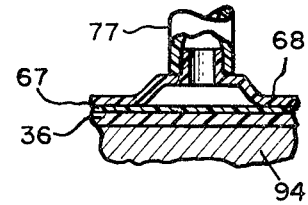
FIG. 14 is a cross-sectional view of a connector fitting of the fluid circuit taken along line 14—14 of FIG. 11.

The connector element 77, which is identical in construction to connector elements 73–76, is seen in FIG. 14 to comprise a short conduit segment 154 having an outside diameter corresponding to the inside diameter of tubing segment 31. The tubing segment is forced over one end of the conduit segment, and the other end is bonded to a projecting flange portion 155 of the flexible sheet member 71. A bonding material is applied between the ends of the conduit segment and the sheet member and tubing segment to provide a durable fluid seal.

Figure 15:
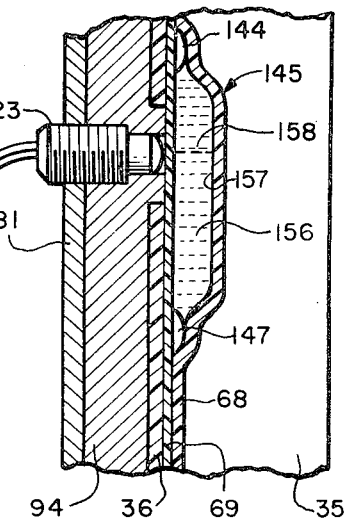
FIG. 15 is a cross-sectional view of the fluid absence detector incorporated in the fluid circuit taken along line 15—15 of FIG. 11.

Referring to FIG. 15, the fluid absence detector 145 comprises a vertically-orientated chamber 156 through which plasma-deficient whole blood flows prior to being reinfused into the patient. When processing module 20 is installed in actuator 21 chamber 156 is vertically aligned, so that should a fluid absence develop, as a result of a pump malfunction, an occlusion, or any other reason, a fluid void will develop at the upper end of the chamber. A fluid detector system comprising the ultrasonic transceiver 123 on actuator plate 94 and a reflecting surface 157 on sheet member 68 sense the presence or absence of whole blood at a predetermined level 158 within chamber 156. Upon the detector sensing a fluid absence at this location, operation of the plasmapheresis processing system is terminated and an alarm is sounded, in accordance with conventional practice. The fluid absence detector, and its associated circuitry may be similar to that described in U.S. Pat. No. 4,341,116 to Arnold C. Bilstad and Michael Wisnienski.

Figure 9:
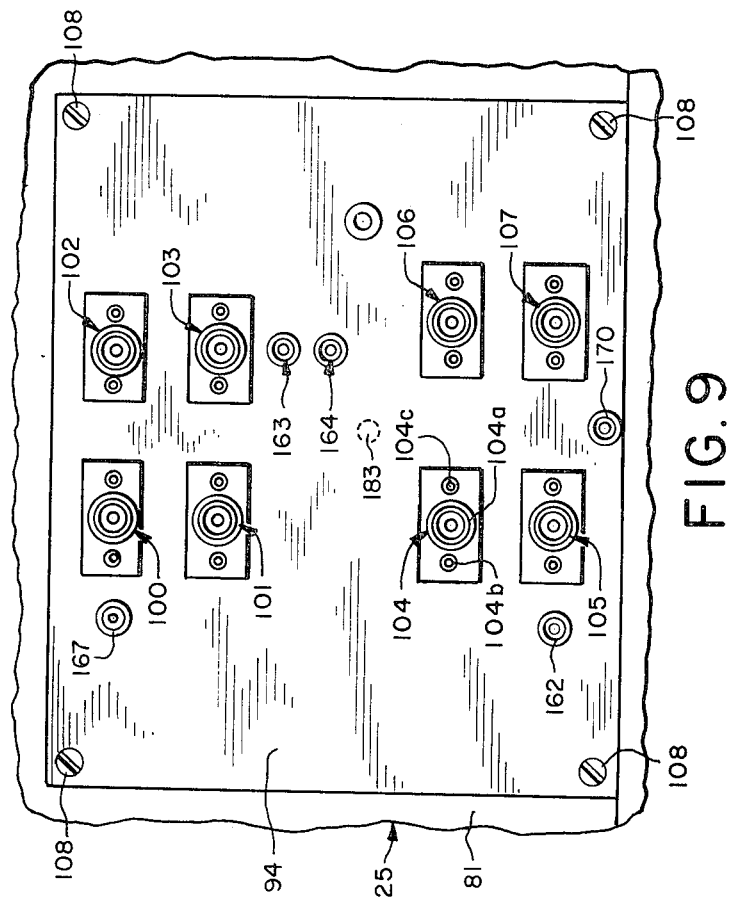
FIG. 9 is a front elevational view of the actuator plate of the processor apparatus.
Figure 16A:
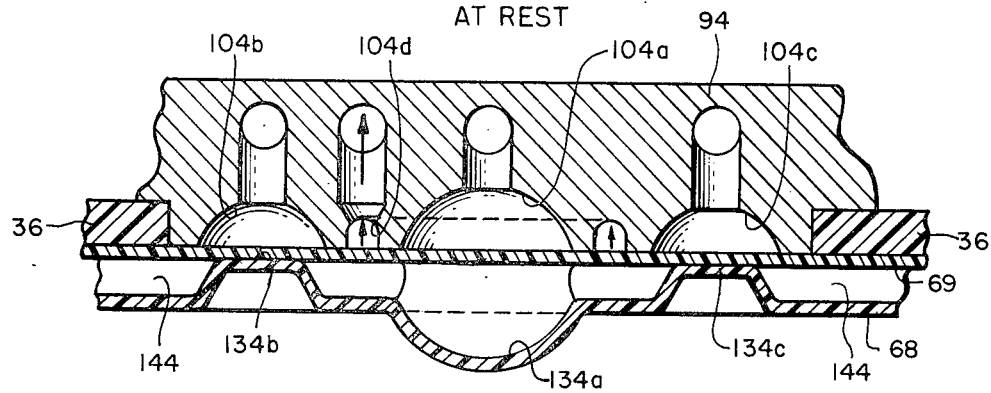
FIGS. 16A-16C are enlarged cross-sectional views of a normally closed pump element of the fluid circuit taken along line 16—16 of FIG. 11 showing the element in at rest, fill and pump conditions, respectively.
Figure 16B:
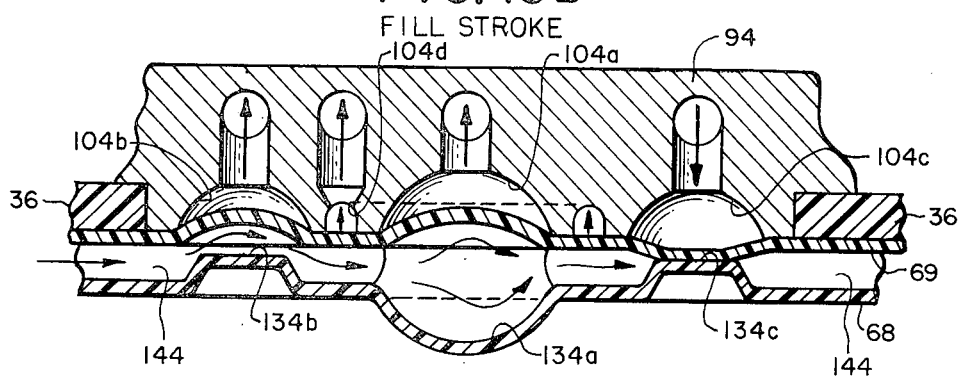
Figure 16C:
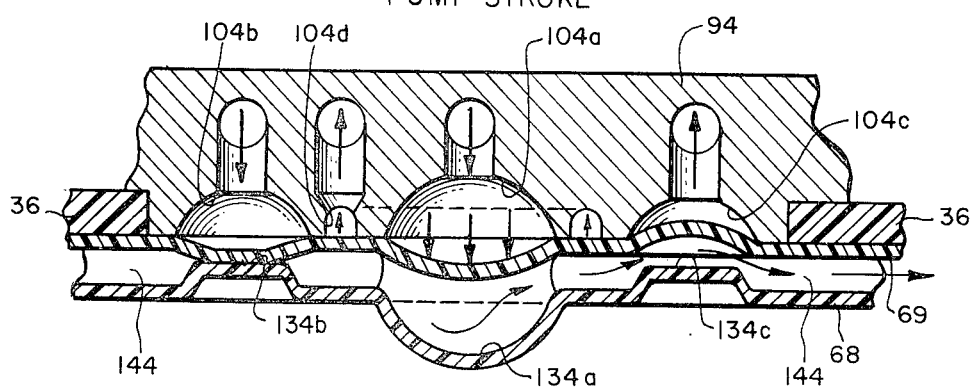

As shown in FIGS. 16A–16C, each of the eight pump elements 130–137 in fluid circuit 129 includes a central displacement chamber (a), an upline valve stop (b), and a downline valve stop (c). As shown in FIG. 9, the eight pump actuator elements 100–107 on actuator plate 94 each include a central pumping port (a), an upline valving port (b), and a downline valving port (c), which interact with the central displacement chamber, upline valve stop, and downline valve stop of their counterpart pump elements in the fluid circuit. In addition, each of the eight pump actuator elements includes an annular hold-down port (d) which encircles the pump actuator port (a).

The operation of pump elements 130–137 is illustrated in FIGS. 16A–16C. As shown in the figures, the inlet valve consists of an actuator port 104b formed in actuator plate 94 of the station 24, and a valve stop 134b formed in the rigid sheet member 68. Similarly, the outlet valve consists of an actuator port 104c and a valve stop 134c. Each pump chamber is formed by a pump port 104a in the actuator plate and a displacement chamber 134a in the bottom panel.

At rest, as shown in FIG. 16A, processor apparatus 21 provides no vacuum at either the upline valving chamber 104b or the downline valving chamber 104c. Consequently, sheet member 71 rests in contact with the inlet and outlet valve seats 134b and 134c. This condition may be enhanced by providing a positive pressure at valving chambers 104b and 104c.

During operation of the system, a pump fill stroke is initiated by processor apparatus 21 by drawing a vacuum in inlet valving chamber 104b to draw sheet member 71 into the valving chamber. This opens the inlet valve and allows fluid to flow through the valving chamber and into the displacement chamber 134a. At this time a vacuum is slowly drawn at the pumping port 104a so as to draw the sheet member 71 to the bottom (as viewed in FIG. 16B) of the displacement chamber to cause fluid to enter the chamber. At this time the downline valve is closed by reason of a positive pressure being applied at valving port 104c, causing sheet member 71 to be displaced against the valve stop 134c.

Upon completion of the fill stroke a pump stroke is initiated by processor apparatus 21. Inlet valving port 104b is pressurized to displace sheet member 71 against valving shoulder 134b. At the same time, a vacuum is drawn at outlet valving port 104c to draw sheet member 71 into the valving port thereby opening the outlet valve. A positive pressure is next slowly introduced into pumping port 104a to force sheet member 71 upwardly (as viewed in FIG. 16C) to displace fluid within the fluid displacement chamber 134a.

Figure 17A:
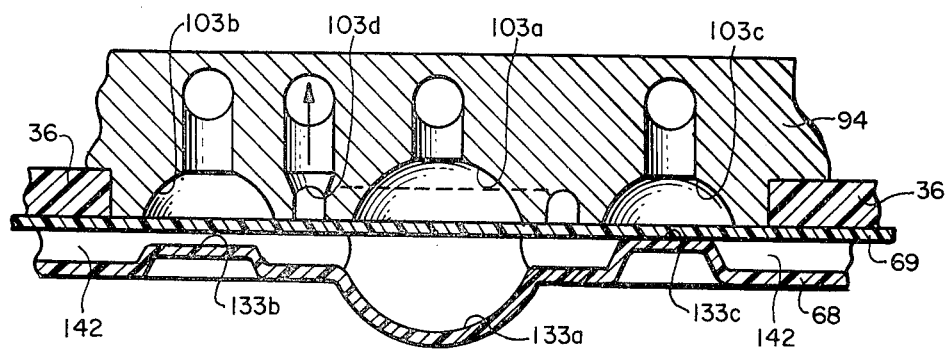
FIGS. 17A-17C are enlarged cross-sectional views of a normally-open pump element of the fluid circuit taken along line 17—17 of FIG. 11 showing the element in at rest, fill and pump conditions, respectively.
Figure 17B:
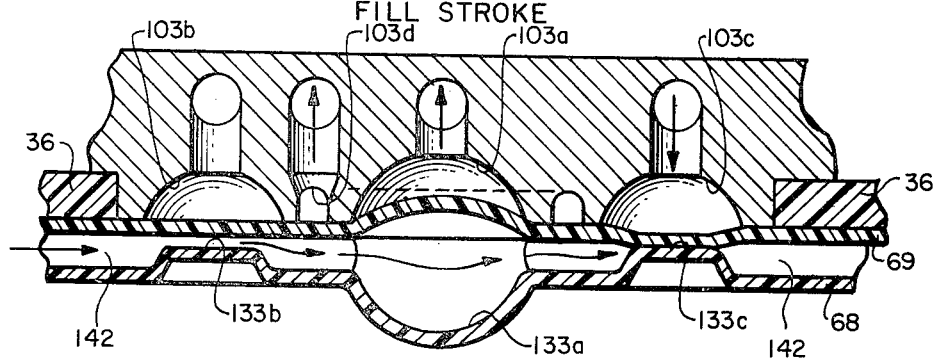
Figure 17C:
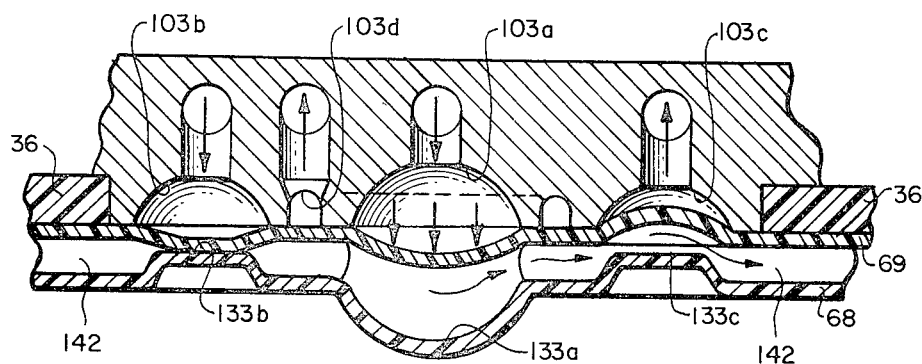

An alternate construction for the pump elements is shown in FIGS. 17A–17C, which depict the construction and operation of the ACD pump element 133. Instead of a normally closed inlet valve stop 134b provided in pump element 134, valve 133 utilizes a normally open valve stop 133b which is closed only during the pump stroke upon application of positive pressure to the inlet valve control port 103b, as shown in FIG. 20c. By avoiding the need to draw a vacuum in inlet valve control port 103b during rest and fill strokes valve element 133 conserves energy within the apparatus and simplifies the associated valve actuator apparatus.

The pump chamber 133a and outlet valve 133c of valve 133 are identical in construction and operation to those of valve 134. Outlet valve 133c is closed by positive pressure during the fill stroke, and opened by negative pressure and/or fluid pressure during the pump stroke. The pump element actuator ports 103a–103d are identical to those of valve 134.

Another alternate construction for the pump elements is shown in FIGS. 18A–18E, which depict the construction and operation of the bidirectional saline pump element 136. This pump element ultilizes two normally or partially open valve elements 136b and 136c, which can be actuated by appropriate pressures through pressure ports 106b and 106c respectively. As shown in FIG. 20a, at rest both valves are open and fluid can flow through the pump element.

Figure 18A:
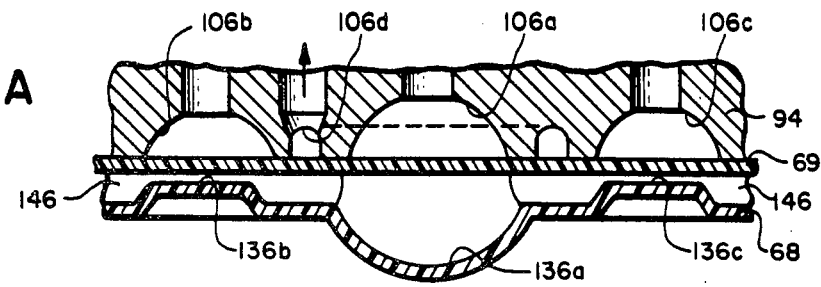
FIGS. 18A-18E are enlarged cross-sectional views of a bidirectional pump element of the fluid circuit taken along line 18—18 of FIG. 11 showing the element in at rest, fill and pump conditions in one direction, and in fill and pump conditions in the other direction, respectively.
Figure 18B:
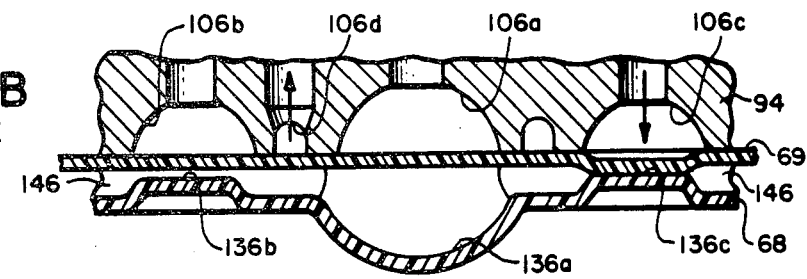
Figure 18C:
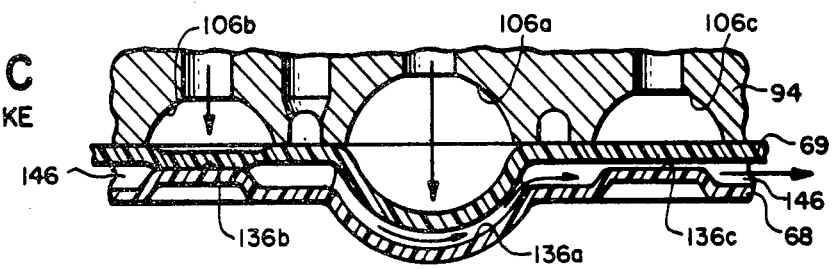
Figure 18D:
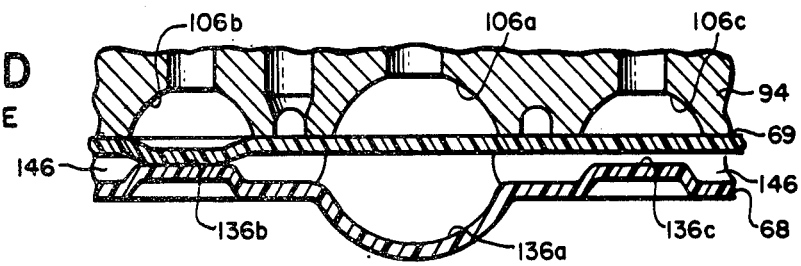
Figure 18E:
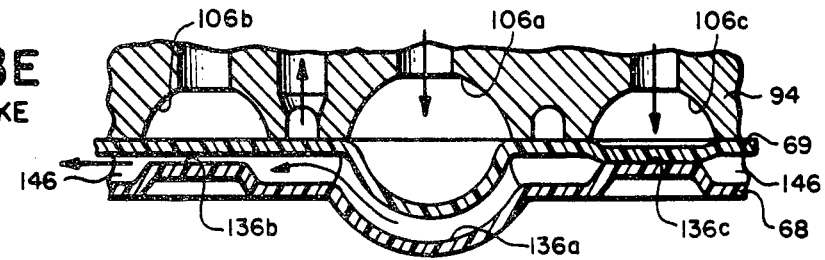

For left-to-right flow, as illustrated in FIGS. 18B and 18C, valve 136b is open during each fill stroke, and closed by positive pressure at port 106b during each pump stroke. At the same time, valve 136c is closed by pressure applied through port 106c during each fill stroke, and allowed to remain open during each pump stroke. For right-to-left flow, as illustrated in FIGS. 21d and 21e, valve 136b is closed during each fill stroke, and valve 136c is closed during each pump stroke.

Thus, valve element 136 is able to pump fluid in either direction, with a minimal pressure requirements for valve actuation. This makes the valve construction well suited for use in the saline conduit 146, where flow may take place into the system during normal replacement procedures, and out of the system during prime and purge procedures.

Figure 19:
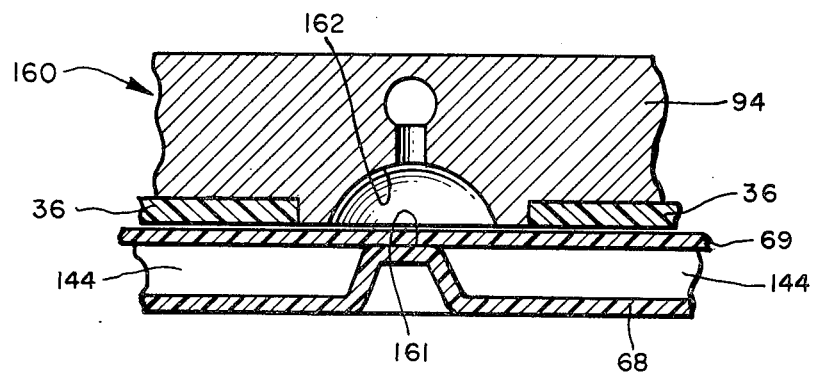
FIG. 19 is a cross-sectional view of a pressure regulator element of the fluid circuit taken along line 19—19 of FIG. 11.

For optimum efficiency in separating plasma it is desirable that the transmembrane pressure (TMP) present in the hollow-fiber filter element 141 be controlled and regulated. To this end, the fluid circuit 129 includes in-line in conduit segment 144 a pressure regulator element 160. Referring to FIG. 19, this regulator comprises a valve stop 161 in the rigid bottom panel 36 and an underlying pressure port 162 in actuator plate 94. With this arrangement it is necessary that the flexible sheet member 71 be deflected downwardly into pressure port 162 and away from valve stop 161 before fluid can flow through conduit 144. Pressure regulation is provided by introducing a predetermined metering pressure in chamber 162 in opposition to deflection of sheet member 71, so that the valve opens only when the desired pressure level has been reached in conduit 144, and modulates to maintain the desired pressure once flow has been initiated. By maintaining the metering pressure constant, the desired upline pressure is maintained in conduit 144 and filter element 141.

In some applications it may be possible to avoid the need for pressure regulator element 160 by appropriately biasing the normally-closed inlet valve chambers 134b and 135b so that pump elements 134 and 135 function as pressure regulating elements. The outlet valves 134c and 135c would then remain unbiased by pneumatic pressure so as to open in response to applied fluid pressure upon the opening of inlet valves 134b and 135c.

To permit the monitoring of system operating pressures, fluid circuit 129 includes three pressure monitor elements 163–165. Pressure monitoring element 163 is located in conduit segment 163 and monitors negative pressure to detect the occurrence of a collapsed vein. Monitor 164 is located in conduit segment 144 and monitors positive pressure to detect the occurrence of an occlusion in the output circuit. Monitor 165 is located in the input conduit 40 to the filter element 141 to monitor filter inlet pressure, and hence TMP.

Figure 20:
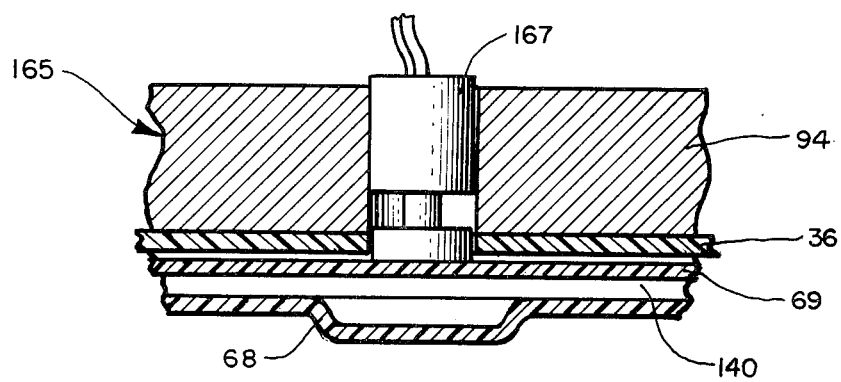
FIG. 20 is a cross-sectional view of a pressure sensor element of the fluid circuit taken along line 20—20 of FIG. 11.

Referring to FIG. 20, sensor element 165, which may be identical to elements 163 and 164, is seen to comprise an in-line chamber 166 formed in conduit segment 140, and a conventional pressure transducer 167 mounted within actuator plate 94 and positioned to operatively engage the flexible sheet member as it overlies the chamber. Pressure variations in the fluid, which necessarily exist in the chamber, are reflected in changes in the electrical output signal produced by transducer 167. These signals are utilizes by appropriate control circuitry in actuator apparatus 21 to provide readouts of system parameters and to control the operation of the fluid circuit.

Figure 21:
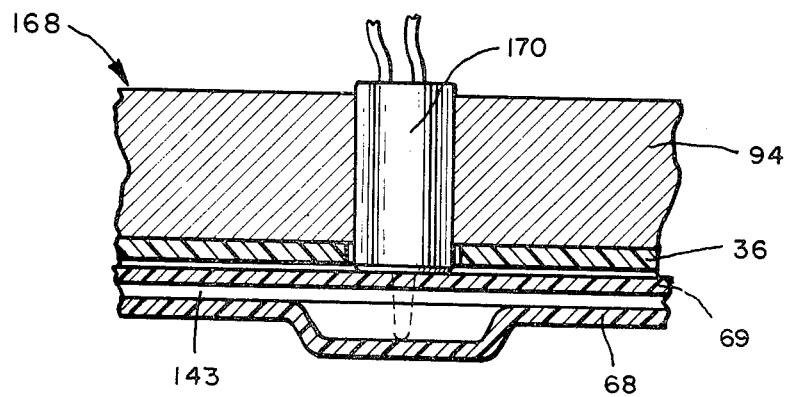
FIG. 21 is a cross-sectional view of a hemolysis detector element of the fluid circuit taken along line 21—21 of FIG. 11.

To prevent red blood cells from being inadvertently collected in plasma collection container 30, the fluid circuit 129 includes a hemolysis detector 168 in conduit segment 143. Basically, as shown in FIG. 21, this detector includes an in-line chamber 169 through which collected plasma is caused to flow. The presence of red blood cells in this chamber is detected by a detector 170, which may include two monochromatic light sources of different frequencies, a light detector responsive to reflection of light from within the chamber, at the two frequencies, and circuitry responsive to the light detector for providing an alarm. The detector system may be as described in U.S. Pat. No. 4,305,659 to Arnold C. Bilstad et al.

To maintain a continuous non-pulsating flow through the fluid circuit, the paired fluid pump elements are operated in alternation. That is, when one pump component is operated in a fill stroke, its pair is operating in a pump stroke. In this way, an uninterrupted non-pulsating flow of fluid is maintained through the fluid circuit.

Specifically, elements 132 and 133 are paired and operated to introduce ACD into the main fluid conduit 140 at an operator-designated rate to prevent blood clotting. Pump elements 130 and 131 advance the whole blood obtained from the donor together with the ACD to the hollow fiber filter element 141. Within this element the whole blood is fractionated and the derived plasma component is discharged through conduit segment 143 to the plasma collection container 30.

The plasma-deficient output from filter 141 is advanced along conduit segment 144 by pump elements 134 and 135, which operate in alternation to maintain a smooth nonpulsating flow at this point. Pump elements 136 and 137 introduce saline into the main flow conduit 144 at an operator-designated rate as a plasma replacement fluid, or pump fluid and/or trapped air into saline container 44 during prime and purge procedures.

By controlling the rate at which pressure differentials are established in the pump actuator ports 100a-107a a gentle and natural pumping action is obtained which provides minimal damage to processed blood cells. The pumping rates of the individual pump elements may be set by the operator, or by automatic means within the processor apparatus responsive to measured system parameters, such as the volume and rate of plasma collection. To this end, control panel 26 (FIGS. 6 and 7) of apparatus 21 includes a selector switch 171 by which the operating speed of the anticoagulant pump element is set, a potentiometer control 172 and digital readout 173 by which the operating speed of whole blood pump elements 130, 131 and 134, 135 is controlled, and a potentiometer 174 and digital readout 175 by which the operating speed of the replacement fluid pump element 136, 137 is controlled. A plurality of push button switches 176 are provided to establish the operating mode of the apparatus, and a plurality of status-indicating lights 177 provide indications of malfunctions in the system. A digital readout 178 indicates the total volume of plasma collected, and a digital readout 179 indicates plasma collection rate. A selector switch 180 enables the replacement fluid rate to be set as a ratio of the actual plasma collection rate.

Since the displacement chambers 130a-137a each of the pump elements 130-137 have a fixed and constant volume, fluid flow within the fluid circuit 129 can be controlled with great accuracy by controlling the number of pump actuations. Since each pump pulse may be treated as an aliquot, processing, proportioning and timing operations are easily accomplished in the course of the procedure.

In many procedures, such as continuous flow blood fractionation, or hemodialysis, it is desirable that the fluid being processed in fluid module 20 be maintained at a constant predetermined temperature, such as 98° F. To this end, processor apparatus 21 may, as shown in FIG. 8, include a resistance heating element 181 in actuator plate 94, in addition to appropriate thermal insulation for this component. This element is powered by suitable circuitry within the processor apparatus in accordance with the temperature sensed by a temperature sensing element 183 on actuator plate 94 to maintain the desired temperature. Because of the minimal fluid volume in process at any one time, and the intimate contact between the fluid circuit 129 and the relatively massive actuator plate 94, efficient thermal transfer is realized and fluid temperature is accurately maintained.

Alternatively, where it is desired that the fluid in process be cooled, as in cryoagulation procedures, or in the secondary treatment of plasma, cooling elements may be substituted for heating element 181, and a necessary amount of cooling provided as sensed by temperature sensor 183.

Furthermore, while the ACD and saline containers 43 and 44 have been shown as discrete containers, it will be appreciated that with appropriate modifications to fluid circuit 129, such as the provision of valves inline with the containers, these containers as well as containers for any other fluid, stored or collected in a procedure, could be formed directly within the fluid circuit, with a construction similar to that of chamber 150 of filter element 141.

Also, while the filter element 141 has been shown as formed within the fluid circuit, it will be appreciated that if desired this element can be provided as a discrete element, apart from the fluid circuit. Connections to the element would then be made by tubing segments, as containers 43 and 44.

Figure 22:
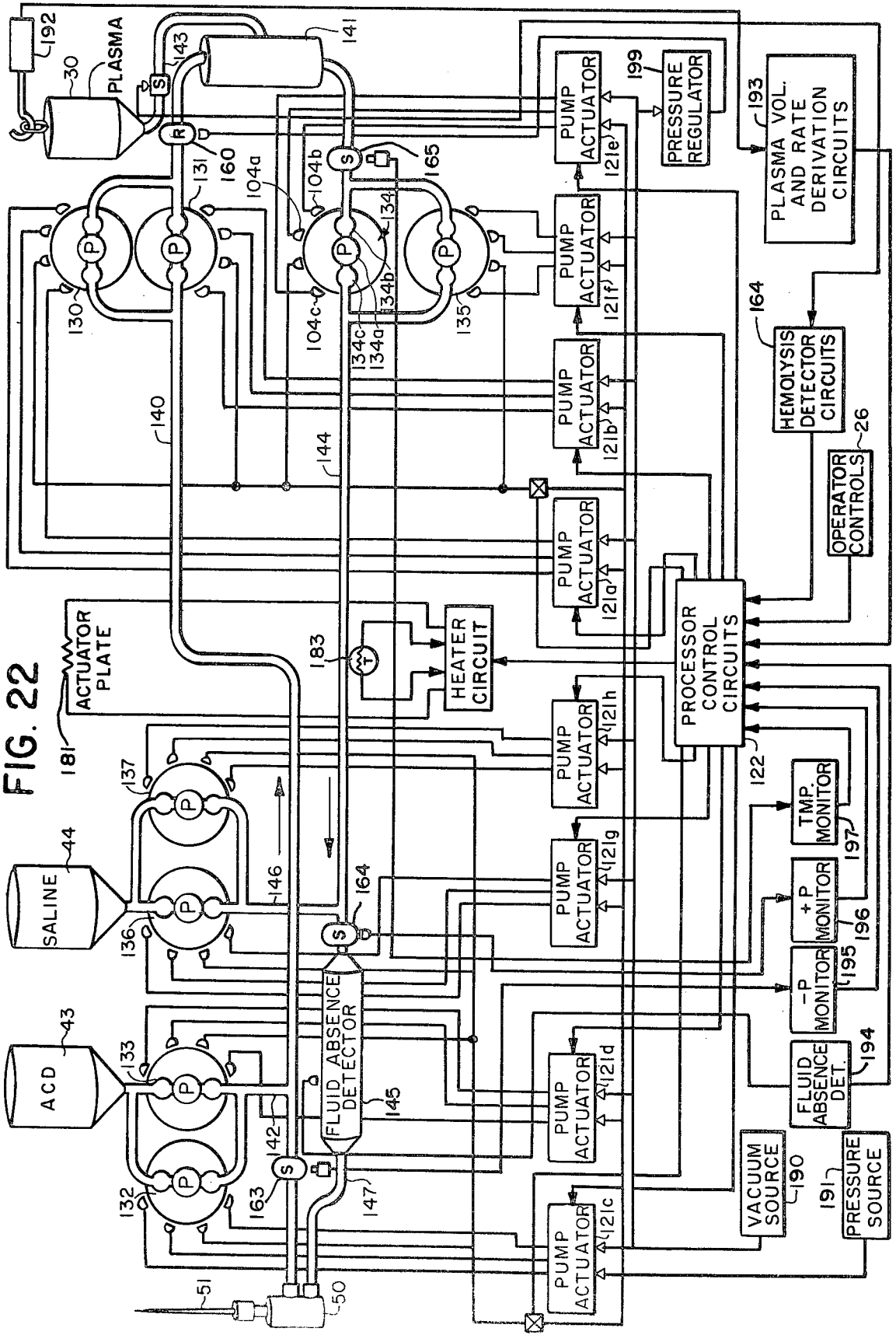
FIG. 22 is a functional block diagram partially in schematic form of the control and actuator circuits of the processor apparatus.

Referring to FIG. 22, within the processor apparatus 21 each of the pump elements 130-137 has associated with it a respective one of eight pump actuator circuits 121a-121h. These pump actuators are arranged to provide a proper sequence of fill and pump strokes by supplying appropriate vacuum and/or pressure differentials to the pumping and valving ports associated with the pump elements. A single vacuum source 190 and a single pressure source 191, provide pressure differentials to each actuator circuit. Appropriate solenoid-controlled valves within the actuator circuits control the application of vacuum and pressure from these sources to the individual pump and valve chambers.

The initiation of each pump cycle by each pump actuator is controlled by application to the pump actuator of a pump command signal. To establish the rate at which the respective pairs will pump the respective fluids through the fluid circuit, the processor control circuits 122 provide pump cycle control signals for application to each pump actuator stage. The processor control circuits 122 respond to operator designation of pump rates, as provided at control panel 26, as well as other system variables. One such system variable is the rate of plasma collection, which is monitored by a weight transducer 193 which provides an output signal indicative of the weight of the plasma collection container 30 and the plasma collected therein. This signal is converted by collection volume and rate derivation circuits 193 to a collection rate signal which is applied to processor control circuits 122. Processor circuits 122 respond to the signal to adjust the flow rate through the fluid circuit for optimum performance of the hollow fiber filter element 141.

The operation of the rate and volume derivation circuits 193 is described and claimed in the copending applications "Blood Fractionation Apparatus Having Collected Volume Display System", Ser. No. 330,899, filed Dec. 15, 1981, and now U.S. Pat. No. 4,458,539 and "Blood Fractionation Apparatus Having Collection Rate Display System", Ser. No. 330,901, filed Dec. 15, 1981 and "Blood Fractionation Apparatus Having Replacement Fluid Ratio Control System", Ser. No. 330,900, filed Dec. 15, 1981. Reference is made to these applications for a further description of the operation of the rate and volume derivation circuit.

Additional sensing inputs are provided by the fluid absence detector 145, which provides an output signal to processor control circuits 122 through sensing circuits 194 upon the occurrence of a fluid absence, and pressure detectors 163–165, which provide output signals through sensing circuits 195–197 indicative of selected fluid circuit pressures. Control circuit 122 utilizes to these inputs, and the output of hemolysis detector 168, through a sense circuit 199 to vary pumping and valving functions for optimum efficiency, and for interrupting operation in the event of a system malfunction.

Reference is made to the previously-identified copending application of the present inventors, entitled "Prepackaged Fluid Processing Module Having Pump and Valve Elements Operable in Response to Externally Applied Pressures", filed concurrently herewith, for a further explanation of fluid module 20.

By reason of the compact fluid circuit made possible by the processor apparatus of the invention, fluid connections between elements of the fluid module are short and direct, so that, in the case of plasmapheresis, a minimal quantity of blood is removed at any one time from the donor during processing. This minimizes trauma to the donor.

Furthermore, by reason of the pumping and valving connections being automatically established by the processing apparatus upon installation of the module housing, set-up time is minimized, to the benefit of both the operator and the donor.

While a particular embodiment of the invention has been shown and described, it will be obvious to those skilled in the art that changes and modifications may be made without departing from the invention in its broader aspects, and, therefore, the aim in the appended claims is to cover all such changes and modifications as fall within the true spirit and scope of the invention.

We claim:

1. Fluid processing apparatus for use in conjunction with a fluid module of the type including a housing having an access port in a panel thereof;
   a first relatively-inflexible fluid-impermeable sheet member positioned within the housing, the first sheet member including an outwardly depressed portion therein which faces the housing panel;
   a second relatively flexible fluid-impermeable sheet member positioned within the housing between the first sheet member and the housing panel, the second sheet member forming in conjunction with the depressed portion of the first sheet member a fluid circuit including an element actuable by a pneumatic force applied to the second sheet member through the panel access port, said fluid processing apparatus comprising:
   an actuator station for receiving and fixedly positioning said housing; and
   actuator means extending through said panel access port in operative engagement with said second flexible sheet member and including pneumatic port means for applying a pneumatic force to said second sheet member to control fluid flow in the fluid circuit.

2. A fluid processing apparatus as defined in claim 1 wherein said fluid circuit element comprises a pump element operative in response to an applied pneumatic pressure for urging fluid through the circuit, and wherein said pneumatic port means is operative for applying pneumatic pressure to said second sheet member to operate the pump element.

3. A fluid processing apparatus as defined in claim 1 wherein said actuator means include a plurality of pressure port assemblies for contact with portions of said flexible sheet member.

4. A fluid processing apparatus as defined in claim 1 wherein said pneumatic force is applied by said pneumatic port means through the panel access port at a predetermined location on said second sheet member and wherein said housing panel comprises alignment means for maintaining said second sheet member location in operative alignment with said pneumatic port means.

5. Fluid processing apparatus for use in conjunction with a disposable flow module of the type including a housing having a bottom panel with an access aperture therein and at least one side panel, a first relatively inflexible fluid-impermeable sheet member positioned within the housing, the first sheet member having an outwardly depressed portion therein which faces the bottom panel, and a second relatively flexible fluid-impervious sheet member positioned within the housing between the first sheet member and the bottom panel and forming in conjunction with the first sheet member a fluid circuit, said fluid processing apparatus comprising:
   an actuator station for receiving and fixedly positioning said disposable module housing;
   an actuator head within said actuator station arranged for engaging said second sheet member through said access aperture of the bottom housing panel of the module, said actuator head including at least one pressure actuator port; and means for establishing a pressure differential at said actuator port when said actuator head is engaged to control fluid flow through said fluid circuit.

6. A fluid processing apparatus as defined in claim 5 wherein said pressure differential is pneumatically applied.

7. A fluid processing apparatus as defined in claim 5 wherein said fluid circuit element comprises a pump element operative in response to said pressure differential for urging fluid through the circuit.

8. A fluid processing apparatus as defined in claim 5 wherein said actuator head includes a plurality of said actuator ports, and
wherein said pressure differential establishing means is operative for selectively establishing a pressure differential at each of said actuator ports.

9. Fluid processing apparatus for use in conjunction with a fluid module of the type including a housing having an access port in a panel thereof, a first relatively-inflexible fluid-impermeable sheet member positioned within the housing, the first sheet member including an outwardly depressed portion therein which faces the housing panel, and a second relatively flexible fluid-impermeable sheet member positioned within the housing between the first sheet member and the housing panel, the second sheet member forming in conjunction with the depressed portion of the first sheet member a fluid circuit including an element actuable by pressure applied to the second sheet member through the panel access port, said fluid processing apparatus comprising:
an actuator station for receiving and fixedly positioning said module housing, said actuator station including a pressure port assembly extending through the panel access port in operative engagement with the second flexible sheet member for applying pressure to the second sheet member to control fluid flow in the fluid circuit.

10. A fluid processing apparatus as defined in claim 9 wherein said actuator station includes a plurality of pressure port assemblies each in contact with portions of said second flexible sheet member.

11. A fluid processing apparatus as defined in claim 9 wherein said fluid circuit element comprises a pump element operative in response to applied pressure for urging fluid through the circuit.

* * * * *